United States Patent [19]

Traunecker et al.

[11] Patent Number: 4,499,106

[45] Date of Patent: Feb. 12, 1985

[54] LIPOLYTIC COMPOSITION AND METHOD OF TREATING OBESITY

[75] Inventors: Werner Traunecker, Münster-Sarmsheim; Wilhelm Frölke, Ingelheim am Rhein; Heinrich Kreuzer, Gau-Algesheim; Hans P. Köllmer, Wackernheim, all of Fed. Rep. of Germany

[73] Assignee: Boehringer Ingelheim KG, Ingelheim am Rhein, Fed. Rep. of Germany

[21] Appl. No.: 496,457

[22] Filed: May 20, 1983

[30] Foreign Application Priority Data

Jun. 1, 1983 [DE] Fed. Rep. of Germany ....... 3220598

[51] Int. Cl.$^3$ ............................................. A61K 31/16
[52] U.S. Cl. .................................................... 514/603
[58] Field of Search ......................................... 424/320

[56] References Cited

U.S. PATENT DOCUMENTS 4,038,314  7/1977  Mentrup et al. ................ 260/556 N

*Primary Examiner*—Stanley J. Friedman
*Attorney, Agent, or Firm*—Hammond & Littell, Weissenberger & Dippert

[57] ABSTRACT

Lipolytic pharmaceutical composition containing 1-(4-hydroxy-3-dimethylamino-sulfonamidophenyl)-1-hydroxy-2-(1-phenoxy-isopropylamino)ethane or a pharmaceutically acceptable acid addition salt thereof as the active ingredient, and a method of combatting obesity therewith.

1 Claim, No Drawings

LIPOLYTIC COMPOSITION AND METHOD OF TREATING OBESITY

This invention relates to pharmaceutical compositions which contain as the active ingredient the compound 1-(4-hydroxy-3-dimethylamino-sulfonamido-phenyl)-1-hydroxy-2-(1-phenoxy-isopropylamino)ethane (Me 693), and to a method of treating both generalized and also localized obesity in warm-blooded animals therewith.

BACKGROUND OF THE INVENTION

It is known from West German Pat. No. 2,115,926 that a group of sulfonamides, which includes 1-(4-hydroxy-3-dimethylamino-sulfonamidophenyl)-1-hydroxy-2-(1-phenoxy-isopropylamino)ethane (Me 693), having a dilating effect upon the peripheral blood vessels, influence blood pressure, increase the capacity of the heart, and have broncholytic properties.

Compounds which exhibit activities of this kind are known as $\beta$-adrenergics. Known $\beta$-adrenergics have, in addition to the properties mentioned above, a marked glycogenolytic effect on the skeletal muscle, which is accompanied by lactacidemia.

DESCRIPTION OF THE INVENTION

We have discovered that 1-(4-hydroxy-3-dimethylamino-sulfonamidophenyl)-1-hydroxy-2-(1-phenoxy-isopropylamino)ethane (Me 693), alone in this series of compounds, has a significantly different effect on the metabolism from the other $\beta$-adrenergics. Namely, it does not have the glycogenolytic effect which is inherent in the other $\beta$-adrenergics; no changes are observed in blood lactate either. On the other hand, the compound is distinguished by a particularly long-lasting selective lipolytic effect, that is, the mobilization of the unesterified fatty acids by the splitting of fatty deposits is well to the fore compared with the splitting of the stored form of the carbohydrates and the occurrence of lactacidemia.

Table 1 below shows that, in comparison with isoprenaline ($\beta_1/\beta_2$ stimulant) and fenoterol (predominantly a $\beta_2$ stimulant), an identical dosage of Me 693 leads to a much higher increase in the unesterified fatty acids in the blood than do the comparison substances. On the other hand, the lactacidemia observed after the administration of isoprenaline and fenoterol is significantly greater than that found after the administration of Me 693. This extremely strong differentiation in the metabolism in favor of the lipolytic activity is exceptionally surprising for a $\beta$-adrenergic.

TABLE 1

Metabolic effects in the blood plasma of fed rats. Measurements in $\mu$mol/l (unesterified fatty acids) and mmol/l (lactate). Averages ± S.E.M. N of the treated groups = 5–6.

| Compound | Dosage mg/kg s.c. | Unesterified Fatty Acids Control Group | Δ% | Lactate Control Group | Δ% |
|---|---|---|---|---|---|
| Me 693 | 0.1 | 692 ± 18 | +34 | 2.61 ± 0.14 | 0 |
|  | 1.0 | N = 11 | +190 | N = 18 | +34 |
| Isoprenaline | 0.1 | 753 ± 3 | +15 | 2.64 ± 0.15 | +112 |
|  | 1.0 | N = 17 | +27 | N = 18 | +148 |
| Fenoterol | 0.1 | 743 ± 4 | +18 | 2.78 ± 0.06 | +33 |
|  | 1.0 | N = 15 | +30 | N = 18 | +109 |
| Me 693 | 1 mg/kg oral | 653 ± 5 N = 15 | +63 |  |  |

Table 2 illustrates a series of pharmacological effects which are specific to $\beta$-adrenergics. If the effects on the heart (heart rate), circulation (diastolic blood pressure, peripheral vasodilation) and bronchi, on the one hand, and the increase in the unesterified fatty acids in the blood after the administration of Me 693, on the other hand, are compared with the effects of isoprenaline and fenoterol, it is clear that the cardiovascular and bronchospasmolytic effects are much greater after administration of the comparison substances than with the Me 693, whereas the reverse is true of the lipolytic effects.

TABLE 2

Metabolic and cardiovascular effects and bronchospasmolytic effects of Me 693, isoprenaline and fenoterol in animals of various types. The table gives the maximum percentage changes compared with control values.

| Compound | Unesterified Fatty Acids Conscious Rat mg/kg s.c | N | Δ% | Heart Rate Anesthetized Dog μg/kg i.v. | N | Δ% | Diastolic Blood Pressure Anesthetized Dog μg/kg i.v. | N | Δ% | Peripheral Vasodilation Anesthetized Dog μg/kg i.a. | N | Δ% | Bronchospasmolysis Anesthetized Guinea Pig μg/kg i.v. | N | % Inhibition of ACh spasm |
|---|---|---|---|---|---|---|---|---|---|---|---|---|---|---|---|
| Me 693 | 0.1 | 5 | +34 | 10 | 3 | +8 | 10 | 3 | −24 | 10 | 5 | −14 | 100 | 4 | 0–2 |
|  | 1.0 | 5 | +190 | 20 | 3 | +5 | 20 | 3 | −23 | 30 | 5 | −15 |  |  |  |
| Isoprenaline | 0.1 | 5 | +15 | 0.1 | 5 | +18 | 0.1 | 5 | −40 | 0.003 | 5 | −24 | 10 | 4 | 76–94 |
|  | 1.0 | 6 | +27 | 1 | 5 | +37 | 1 | 5 | −62 | 0.001 | 5 | −28 |  |  |  |
|  |  |  |  | 10 | 5 | +56 | 10 | 5 | −71 | 0.03 | 5 | −33 |  |  |  |
| Fenoterol | 0.1 | 5 | +18 | 0.1 | 6 | +3 | 0.1 | 6 | −13 | 1 | 6 | −20 | 10 | 8 | 67–100 |
|  | 1.0 | 6 | +30 | 1 | 6 | +27 | 1 | 6 | −33 | 3 | 6 | −28 |  |  |  |
|  |  |  |  | 10 | 6 | +50 | 10 | 6 | −54 |  |  |  |  |  |  |

Table 3 shows the strong lipolytic activity and differentiation with regard to cardiovascular parameters after oral administration of Me 693 to three conscious dogs. A dose of only 0.1 mg/kg of Me 693 gives virtually a 100% increase in the unesterified fatty acids in the blood while the heart rate and the diastolic blood pressure are unaffected. Only at a dosage of 0.3 and 1 mg/kg are there any dose-dependent increases in heart rate and reductions in blood pressure, while the unesterified fatty acids are increased still further to a high level. On the other hand, the lactate values measured at the same time (not shown in the table) remain within the range of the control values. It can thus be assumed that in dogs the lipolytic activity starts significantly below the lowest dose chosen (0.1 mg/kg), and that therefore there is a wide dosage interval before the cardiovascular effects begin.

TABLE 3

Metabolic and cardiovascular effects of Me 693 administered orally to three conscious dogs. The table gives the maximum percentage changes compared with the control values.

| Dosage mg/kg by oral route | Unesterified Fatty Acids Δ% | Triglycerides Δ% | Heart Rate Δ% | Diastolic Blood Pressure Δ% |
|---|---|---|---|---|
| 0.1 | +95 | +18 | 0 | 0 |
| 0.3 | +95 | +10 | +36 | −15 |
| 1.0 | +112 | +37 | +95 | −26 |

The differentiation between lipolytic and cardiovascular effects for Me 693 is also demonstrated by experiments in which calorimetric effects of 0.5 mg/kg of Me 693 administered intravenously to rabbits were investigated. The development and release of heat was increased significantly by the compound. Together with the increased oxygen consumption and higher core temperatures, these findings are evidence of increased metabolism. The simultaneous reduction in the respiratory quotient indicates a metabolic shift towards greater utilization of fat. The slight increase in heart rate and ear temperature (improved circulation) observed at this dosage in rabbits is regarded as a sign of a $\beta$-sympathicomimetic effect of the substance.

To summarize, the animal experiments with Me 693 have given the following results:

1. Strong lipolytic activity, virtually negligible glycogenolytic activity (lactate).
2. Extreme differentiation between the lipolytic and glycogenolytic activities, unusual in $\beta$-adrenergics; the reverse is often the case.
3. Differentiation between lipolytic and other effects typical of $\beta$-adrenergics (for example effects on the heart, circulation and bronchi).

For therapeutic use in humans, Me 693, optionally in the form of a pharmaceutically acceptable acid addition salt, is compounded with excipients conventionally used in galenic pharmacy, preferably to form tablets, coated tablets or capsules for oral administration.

The single effective dose is not more than 10 mg, preferably from 0.5 to 5 mg and is administered three times a day.

The following are examples of pharmaceutical compositions containing Me 693 as active ingredient:

EXAMPLE 1

Coated Tablets

The tablet core composition is compounded from the following ingredients:

| | |
|---|---|
| Me 693 hydrochloride | 5.0 parts |
| Lactose | 30.0 parts |
| Corn starch | 20.0 parts |
| Gelatine | 1.5 parts |
| Magnesium stearate | 0.5 parts |
| | 57.0 parts |

Method:

The active ingredient is mixed with the lactose and the corn starch, and the mixture is granulated by moistening it with an aqueous 10% gelatin solution and passing the moist through a screen with a mesh width of 1 mm. The granulate is dried at 40° C. and passed through the screen again, mixed with the magnesium stearate and compressed into 57 mg-tablet cores. The cores thus obtained are coated in the usual way with a shell applied by means of an aqueous suspension of sugar, titanium dioxide, talc and gum arabic. The finished coated tablets are polished with beeswax.

EXAMPLE 2

Tablets

The tablet composition is compounded from the following ingredients:

| | |
|---|---|
| Me 693 hydrochloride | 3.0 parts |
| Lactose | 50.0 parts |
| Corn starch | 40.0 parts |
| Soluble starch | 6.0 parts |
| Magnesium stearate | 1.0 parts |
| | 100.0 parts |

Method:

The active ingredient and the magnesium stearate are mixed and granulated with an aqueous solution of the soluble starch, the granulate is dried and intimately mixed with the lactose and the corn starch. The mixture is then compressed into tablets weighing 100 mg, each of which contains 3.0 g of the active ingredient.

Instead of Me 693 hydrochloride, the free base or any other pharmaceutically acceptable acid addition salt of this compound may be used in Examples 1 and 2. The amount of active ingredient may also vary within the limits given, and the quantity and type of inert carriers may be varied to suit special requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of combatting obesity in a warm-blooded animel in need thereof, which comprises orally administering to said animal an effective lipolytic amount of 1-(4-hydroxy-3-dimethylamino-sulfanamido-phenyl)-1-hydroxy-2-(1-phenoxy-isopropylamino)ethane or a pharmaceutically acceptable acid addition salt thereof.

* * * * *